United States Patent
Walker et al.

(10) Patent No.: US 6,633,817 B1
(45) Date of Patent: Oct. 14, 2003

(54) SEQUENCE DATABASE SEARCH WITH SEQUENCE SEARCH TREES

(75) Inventors: Michael G. Walker, Sunnyvale, CA (US); James Z. Wang, Mountain View, CA (US); Eldar Y. Giladi, Palo Alto, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/474,929

(22) Filed: Dec. 29, 1999

(51) Int. Cl.$^7$ .......................... G01N 33/48; G01V 3/00; G01G 23/01
(52) U.S. Cl. ............................. 702/19; 702/2; 702/102
(58) Field of Search .............................. 702/19, 2, 102; 361/496

(56) References Cited

U.S. PATENT DOCUMENTS

| | | | |
|---|---|---|---|
| 5,577,249 A | 11/1996 | Califano | ..................... 395/611 |
| 5,701,256 A | 12/1997 | Marr et al. | .................. 364/496 |
| 6,233,571 B1 * | 5/2001 | Egger et al. | |

FOREIGN PATENT DOCUMENTS

| | | | | |
|---|---|---|---|---|
| EP | 0583559 A1 | 2/1994 | ......... | G06F/15/415 |
| JP | 08022475 | 1/1996 | ........... | G06F/17/30 |

OTHER PUBLICATIONS

Gracy, Jerome; et al. (1998) "Automated protein sequence database classification. I. Integration of compositional similarity search, local similarity search, and multiple sequence alignment" Bioinformatics, 14(2), p. 164–173.*

Guan, Xiaojun, et al. (1998) "Domain identification by clustering sequence alignments" Bioinformatics, 14(9), p. 783–788.*

Burkhardt, S., et al., "q-gram Based Database Searching Using a Suffix Array (QUASAR)", Recomb 99, Third Annual International Conference on Computational Molecular Biology, Apr. 11–14, 1999, pp. 77–83.

Califano, A., and Rigoutsos, I., "Flash: Fast Look–Up Algorithm for String Homology", IEEE Comput. Soc. Press, IBM T.J. Watson Research Center, Feb. 9, 1995, pp. 1–22.

Fitch, W.M., Smith, T.F., Waterman, M.S., "Comparative Biosequence Metrics", Journal of Molecular Evolution, Springer–Verlag, vol. 18, pp. 38–46, 1981.

Gusfield, D., "Sequence Databases and Their Uses—The Mother Lode", Cambridge University Press 1997, pp. 370–392.

Gusfield, D., "Algorithms on Strings, Trees, and Sequences", Cambridge University Press 1997, pp. 215–253.

Miller, C., Gurd, I., et al., "A RAPID Algorithm for Sequence Database Comparisons: Application to the Identification of Vector Contamination in the EMBL Databases", BioInformatics, vol. 15, No., 2, pp. 111–121, 1999.

* cited by examiner

Primary Examiner—Kenneth R. Horlick
Assistant Examiner—Young Kim
(74) Attorney, Agent, or Firm—Fenwick & West LLP (57) ABSTRACT

A method and system for generating and searching a tree-structured index of window vectors that represent database sequences comprise a window vector generation module, a tree-structured index generation module, a query sequence partitioning module, and a retrieval component. The window vector generation module partitions a database sequence into a plurality of overlapping windows. Each window has a fixed length W comprising a fixed number of nucleotides, and the offset among windows is determined by a parameter Δ. The window vector generation module then maps each database sequence window into a window vector. The database sequence window vector indicates the frequency of appearance of each k-tuple in the corresponding database sequence window. The tree-structured index generation module then generates a tree-structured index using the database sequence window vectors. The query sequence partitioning module partitions a query sequence into a plurality of windows and maps each query sequence window into a query sequence window vector. Each query sequence window vector is then compared against the tree-structured index to locate the database sequences that are similar to the query sequence. The list of database sequences that are similar to the query sequence is then returned as the result of the search.

28 Claims, 11 Drawing Sheets

The TPR as a function of the window size W and the the distance threshold T. Data has an error rate of 5%.

FIG. 9

The ordinate is the TPR and the abscissa is the distance threshold T. Each graph corresponds to a different window size. Data has an error rate of 5%.

FIG. 10

The log base 10 of the FPR as a function of the window size $W$ and the distance threshold $T$. Data has an error rate of 5%.

FIG. 11

The ordinate is the log base 10 of the FPR and the abscissa is the distance threshold $T$. Each graph corresponds to a different window size. Data has an error rate of 5%.

FIG. 12

The ratio of the number of false positive pairs to the number of true positive pairs. Data has an error rate of 5%.

FIG. 13

The ordinate is the computation time in minutes.
The abscissa is the window size.

FIG. 14

SEQUENCE LISTING

<160> NUMBER OF SEQ ID NOS: 2

<210> SEQ ID NO 1
<211> LENGTH: 13
<212> TYPE: DNA
<213> ORGANISM: Artificial Sequence
<220> FEATURE:
<223> OTHER INFORMATION: Presented for Illustrative Purposes

<400> SEQUENCE: 1
accgttgaca ccc                                                          13

<210> SEQ ID NO 2
<211> LENGTH: 20
<212> TYPE: DNA
<213> ORGANISM: Artificial Sequence
<220> FEATURE:
<223> OTHER INFORMATION: Presented for Illustrative Purposes

<400> SEQUENCE: 2
aaccggttac gtacgtggaa                                                   20

SEQUENCE DATABASE SEARCH WITH SEQUENCE SEARCH TREES

BACKGROUND

A. Field of the Invention

The present invention relates generally to storage, indexing, and retrieval of database sequences, and more particularly to a method and system for generating and searching a tree-structured, index of window vectors that represent database sequences.

B. Background of the Invention

Sequence-similarity finding programs identify sequences in DNA and protein databases that are similar to a query sequence. Because of the recent explosion in the amount of DNA sequence information available in public and private databases as a result of the human genome project and other large-scale DNA sequencing efforts, such sequence-similarity finding programs have become increasingly important in modem biology.

Generally, there are two classes of sequence-similarity searching programs: global comparison methods (e.g. Needleman and Wunsch), and local comparison methods, e.g., the FASTA method (Pearson and Lipman), and the BLAST method (Altschul). Global comparison methods have a high degree of accuracy but are extremely slow. Local comparison methods such as FASTA and BLAST identify candidate similar sequences based on shared k-tuples and therefore are faster than global methods. However, local comparison methods are less accurate, i.e. they provide results which are not similar. Moreover, with both the global and local comparison methods, the computational complexity of such methods usually increases linearly with the size of the number of sequences to be searched. This is due in part to the fact that most prior art methods search all, or at least a very large part, of the sequence database. To improve the searching time, several prior art methods have created sequence databases using clusters of sequences, including tree-structured indexes. However, many of these methods use conventional sequence alignment methods such as BLAST and FASTA to determine pairwise distances between the sequences. Thus, such cluster and tree-structured methods are also limited by the speed of the alignment methods described above.

Accordingly, what is needed is a system and method for organizing and searching database sequences that is fast and efficient, and at the same time provides a high degree of accuracy, that is, one that identifies sequences similar to a query sequence.

SUMMARY OF THE INVENTION

The present invention overcomes the limitations of conventional sequence-similarity-searching programs by using window vectors that represent database sequences in a sequence storage and retrieval system. The window vectors associated with the database sequences are organized into a tree-structured index for faster and more efficient searching of the database sequences. A query sequence is used to search the tree-structured index for database sequences that are similar to the query sequence.

In one embodiment, each database sequence is partitioned into a plurality of overlapping windows or fragments of fixed length. Each database sequence window has a fixed length W and the degree of offset between windows is determined by a parameter $\Delta$. Each database sequence window comprises a subsequence of elements from the database sequence beginning at position $j*\Delta$, from the start of the database sequence, and ending at position $j*\Delta+W$, where $j=0, 1, 2, \ldots (L-W)/\Delta$. In other words, each database sequence window has a fixed length W which is advanced down the length of the original database sequence every $\Delta$ elements.

For each database sequence window, a database sequence window vector is computed. A database sequence window vector represents the occurrence of each k-tuple in the database sequence window. In one embodiment, the database sequence refers to a DNA or protein sequence, and the occurrence of each k-tuple in the DNA or protein sequence window is represented by a vector of length $4^k$, Each position in the vector represents a unique k-length sequence (i.e. k-tuple). If a k-tuple occurs more than one time in a database sequence window, either the number of times that the k-tuple occurs may be recorded in the corresponding position in the vector or the value "1" may be recorded in the corresponding position in the vector to indicate that the k-tuple occurs at least once in the database sequence window. If a k-tuple does not occur in a database sequence, a zero in the corresponding position in the vector may be used to indicate that the k-tuple does not occur in the sequence. In one embodiment, database sequence window vectors are stored in a tree-structured index to reduce searching time.

Database sequences are retrieved using a query sequence. In one embodiment, a query sequence is partitioned into a plurality of windows. For each query sequence window, a query sequence window vector is computed. A query sequence window vector represents the occurrence of each k-tuple in the query sequence window. Each query sequence window vector is compared against the tree-structured index of the database sequence window vectors to locate the nearest neighbors of the query sequence, i.e. database sequences similar to the query sequence. In other words, for each query sequence window vector, the tree-structured index is traversed from a root node of the tree to a terminal node which contains the nearest neighbor for that query sequence window vector. In one embodiment, the list of sequences with at least one significant window hit is returned.

In one embodiment, the present invention is used to generate and search a tree-structured index of window vectors that represent biological database sequences. Each database sequence may represent a DNA sequence comprising a fixed number of nucleotides. The DNA database sequence is then partitioned into a plurality of overlapping windows. Each DNA database sequence window has a fixed length W comprising a fixed number of nucleotides, and the degree of offset among windows is determined by a parameter $\Delta$. Each DNA database sequence window is then mapped into a database sequence window vector. The DNA database sequence window vector indicates the frequency of appearance of each k-tuple in the corresponding DNA database sequence window. A tree-structured index is then generated using the DNA database sequence window vectors. To search the tree-structured index, a query sequence (e.g. a DNA sequence) is partitioned into a plurality of windows. Each query sequence window is then mapped into a query sequence window vector. Each query sequence window vector is then compared against the tree-structured index to locate the DNA database sequence window vectors which are closest to the DNA query sequence window vector. The list of DNA database sequences that is similar to the DNA query sequence is then returned.

DETAILED DESCRIPTION OF THE PREFERRED EMBODIMENTS

A. System Overview

Figure 1:
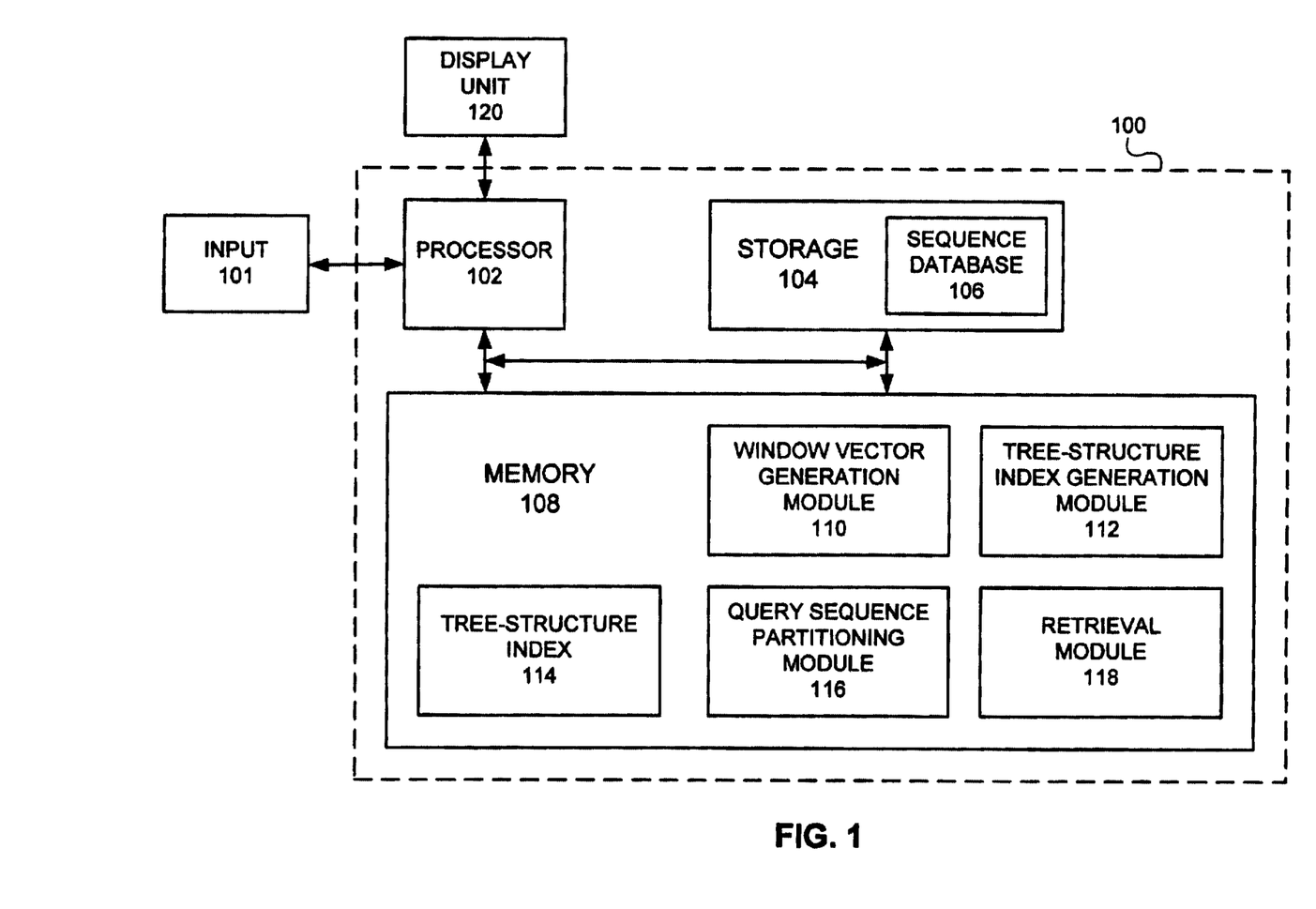
FIG. 1 is a block diagram of a system in accordance with the present invention.

Referring now to FIG. 1, there is shown a block diagram of software and hardware components for implementing one embodiment of the present invention 100. Processor 102 is a conventional engineering workstation or other computer processor and may also be coupled to other processors accessible over conventional communications channels or buses (not shown). Processor 102 is conventionally coupled to storage 104 which may be a magnetic disk storage, a CD storage unit, or other conventional computer data storage unit. Storage 104 may also be coupled to other storage units accessible over conventional communications channels or buses (not shown). Storage 104 includes sequence database 106. Sequence database 106 contains a plurality of sequences, also referred to herein as "database sequences", to be searched. In a preferred embodiment, the database sequences represent biological sequences, such as DNA or protein sequences, that are represented in electronic or computer readable form. The present invention however is not limited to DNA sequences, but may be used with other types of data.

Processor 102 is also conventionally coupled to memory 108 which is a random access memory (RAM) unit or other conventional computer memory. Items in memory 108 may alternatively be stored in storage 104 and accessed by processor 102 when required. Memory 108 may comprise various software products including window vector generation 110, tree-structure index generation 112, tree structure index 114, query sequence partitioning 116, and retrieval 118 program components or modules as discussed below. Input 101 comprises conventional input devices such as a keyboard, mouse, track ball, or touchscreen. A conventional display unit 120 may also be conventionally coupled to processor 102.

In a preferred embodiment, the present invention may be implemented on any platform, operating system, and user interface of sufficient power and flexibility, such as: XWindows/MOTIF; Sun/OS SunView; Microsoft Windows, VAX/VMS, and the like, and may be operated in a distributed data/distributed processor environment, if desired. In a preferred embodiment, the invention is capable of handling a very large data corpus, e.g., containing over 10 million sequences.

Figure 2:
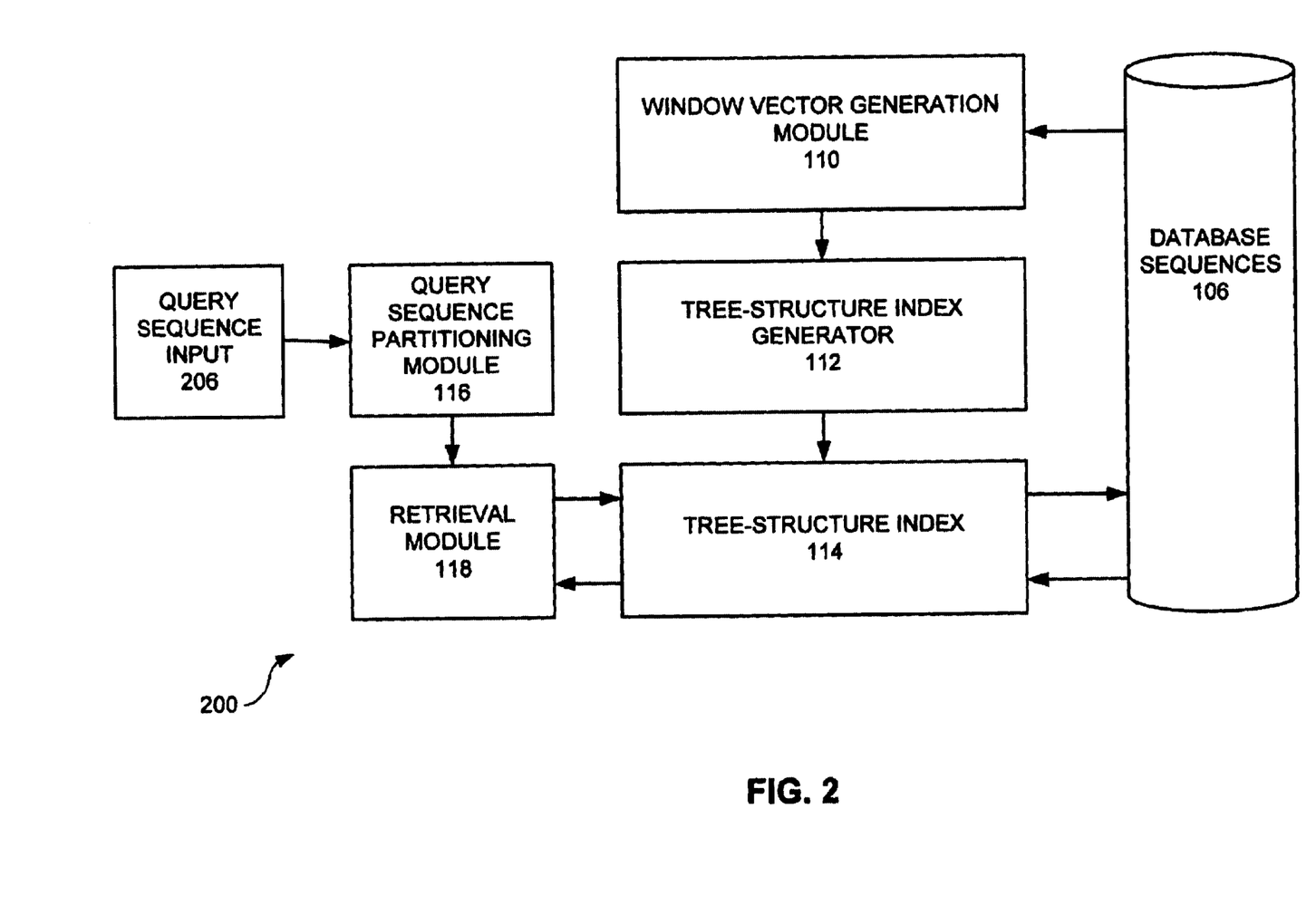
FIG. 2 is a functional block diagram of the present invention.
Figure 3:
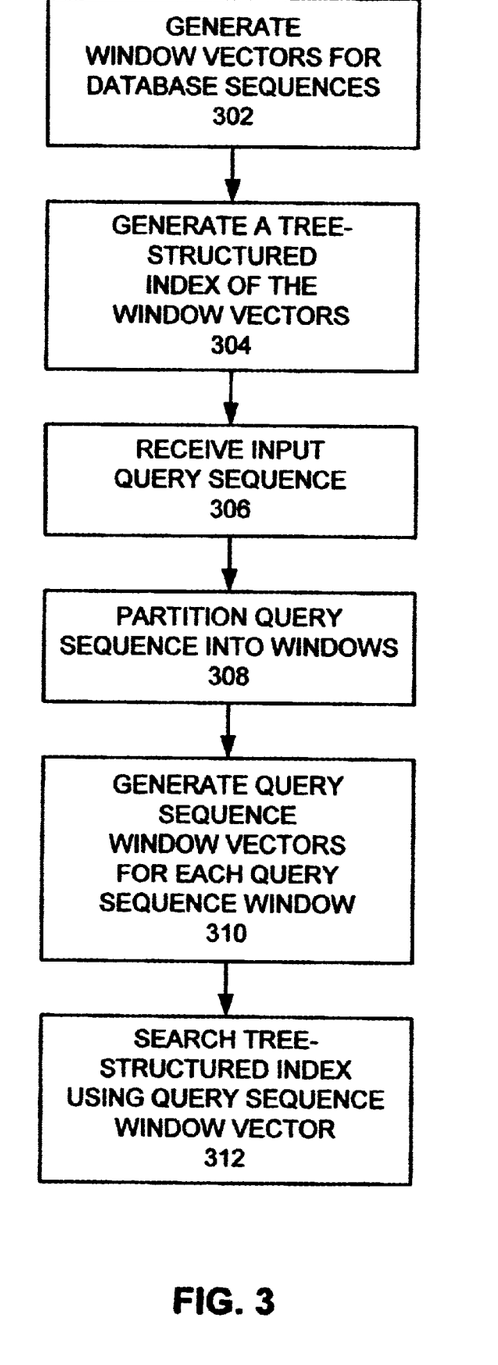
FIG. 3 is a flow chart of the steps of a preferred embodiment of the present invention.

Referring now to FIGS. 2 and 3, there are shown a functional model of the present invention for generating window vectors and identifying database sequences similar to an input query sequence and a flow chart of the steps of a preferred use of the present invention. In this embodiment, the window vector generation module 110 generates 302 a plurality of window vectors associated with each database sequence. Preferably, the window vector generation module 110 partitions each database sequence into a plurality of windows and then encodes each window into a window vector. Preferred embodiments of the functional operation of the window vector generation module 110 are described in more detail below with reference to FIG. 4. The tree-structure index generation module 112 then generates 304 a tree-structured index 114 of the window vectors, preferably using Tree-Structured Vector Quantization (TSVQ). A preferred embodiment of the functional operation of the tree-structure index generation module 112 is described below in more detail with reference to FIG. 7. A query sequence 206 is input 306 into the system, and the query sequence partitioning module 116 partitions 308 the query sequence into a plurality of windows. In a preferred embodiment, the query sequence partitioning module 116 then maps or encodes 310 each query sequence window into a query sequence window vector. A preferred embodiment of the functional operation of the query sequence partitioning module 116 is described below in more detail with reference to FIG. 8. Finally, the retrieval module 118 then uses the query sequence window vector to search 312 the tree-structured index 114 to identify nearest neighbor window vectors for the query sequence, i.e. database sequences which are similar to the query sequence. A preferred embodiment of the functional operation of the retrieval module 118 is described below in more detail with reference to FIG. 8.

Thus, the present invention provides vector quantization and clustering methods for organizing databases for rapid and efficient searching. The present invention is based upon a database sequence search tree where the database sequences are represented using database sequence window vectors organized into a tree-structured index. Window vectors represent the occurrences of each k-tuple of interest in a database sequence, or a query sequence, as described in more detail below. A k-tuple, as used herein, is a fixed length ordered sequence of elements and is well known to one skilled in the art of sequence-similarity searching. The use of window vectors advantageously increases the sensitivity of the present invention as described in more detail below. The database sequence window vectors are then used to generate a tree-structured index representing the database sequences. The tree-structured index decreases the searching time of the present invention by allowing the present invention to search only a portion of the database sequences to find similar sequences. Thus, whereas the searching time required for prior art sequence-similarity searching methods increases linearly with the size of the database, the searching time required for the present invention increases logarithmically with the size of the database.

B. Window Vector Generation

Figure 4:
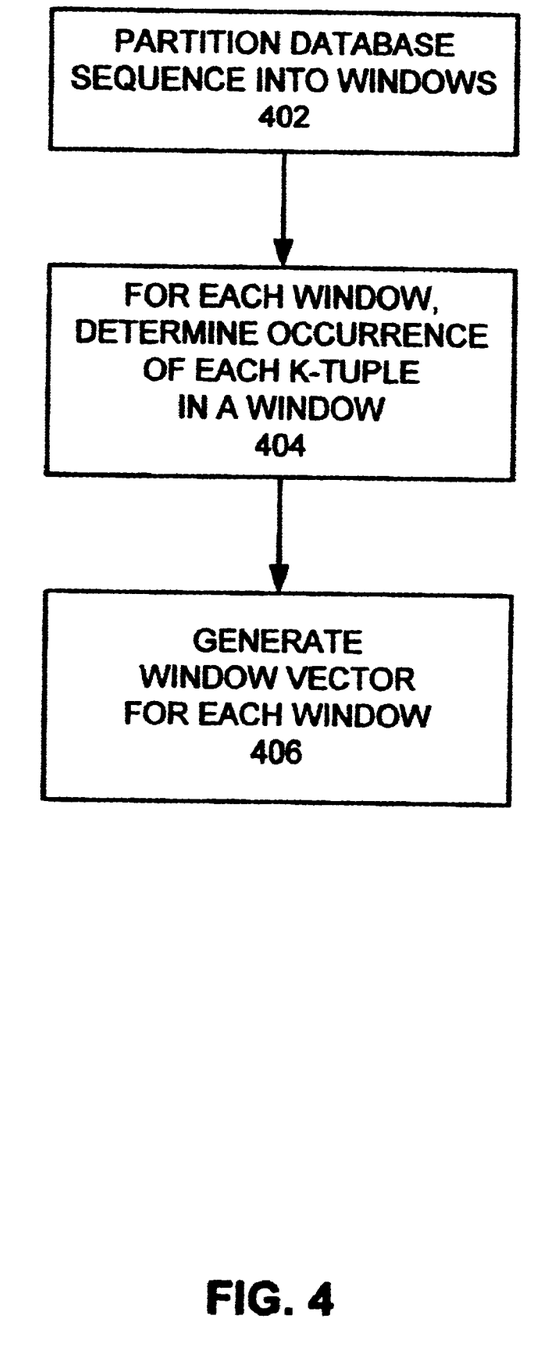
FIG. 4 is a flow chart of the steps of a preferred embodiment for generating window vectors in accordance with the present invention.

Referring now to FIG. 4, there is shown a high-level flowchart of a preferred embodiment of the steps for generating database sequence window vectors in accordance with the present invention. Each database sequence comprises a plurality of elements, L, and is partitioned 402 into a plurality of windows or fragments. Preferably, a "sliding window scheme" is used to partition each database sequence into overlapping windows or fragments. In other words, each database sequence window has a fixed length W and the degree of offset between windows is determined by a parameter $\Delta$. In one embodiment, the length of the window W refers to the number of DNA nucleotides or protein amino acids in the database sequence. Each database sequence window consists of subsequences of the original database sequence beginning t position $j*\Delta$, in the original database sequence, and ending at position $j*\Delta+W$, where $j=0, 1 \ldots (L-W)/\Delta$.

Figure 5:
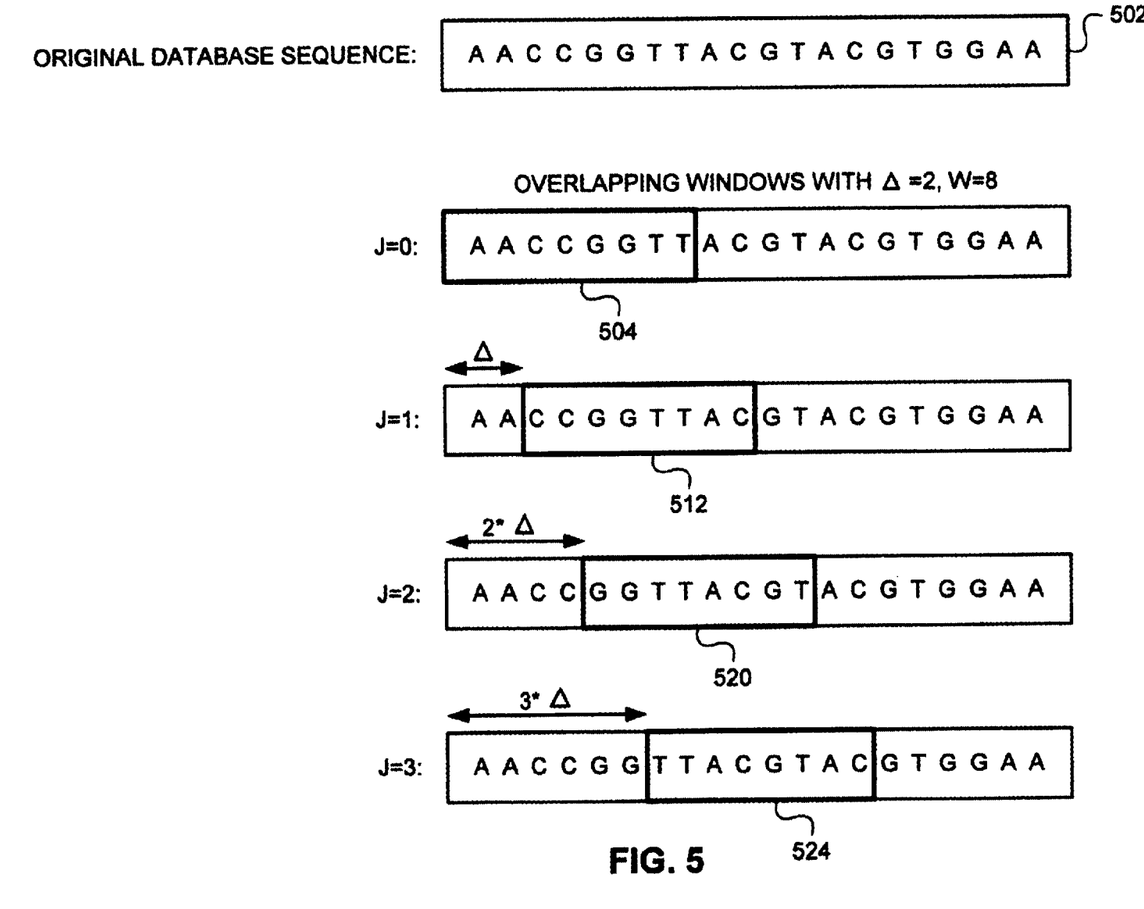
FIG. 5 is an illustration of a preferred embodiment for partitioning a database sequence in accordance with the present invention.

Referring now to FIG. 5, there is shown an example of partitioning a database sequence in accordance with the sliding window scheme. For example, assume an original database sequence 502 comprises a DNA sequence of 20 nucleotides (L=20) where each nucleotide is represented by one of the letters A,C,G, or T. The original database sequence 502 is partitioned into a plurality of windows using the parameters W=8 and $\Delta=2$. Accordingly, for j=0, window 504 is created. For j=1, window 512 is created. For j=2, window 520 is created. For j=3, window 524 is created. The process is continued until all the database sequence windows for the database sequence have been created, that is, until $j=(L-W)/\Delta$ (until j=6 in this example). Thus, for the example in FIG. 5, seven overlapping windows will be generated for the original database sequence 502.

As can be seen in FIG. 5, the offset between each window is a multiple of $\Delta$. For example, the beginning of window 512 is offset from window 504 by $\Delta$ resulting in an overlap of the nucleotides CCGGTT. The beginning of window 520 is offset from window 504 by $2*\Delta$ and from window 512 by $\Delta$. Therefore, between windows 520 and 504 there is an overlap of nucleotides GGTT, and between windows 520 and 512 there is an overlap of nucleotides GGTTAC. Thus, each window has a fixed length W which is advanced down the length, L, of the original database sequence every $\Delta$ elements. In other words, each window runs from $j*\Delta$ to $j*\Delta+W$, where $j=0, 1 \ldots (L-W)/\Delta$. The sliding window scheme is used to generate a plurality of overlapping windows until the end of the DNA database sequence is reached. In a preferred embodiment, values for $\Delta$, W, and L are in the range $0 \geq W \geq 25$; $5 \geq \Delta \geq 50$; and $20 \geq L \geq 1000$.

Figure 6:
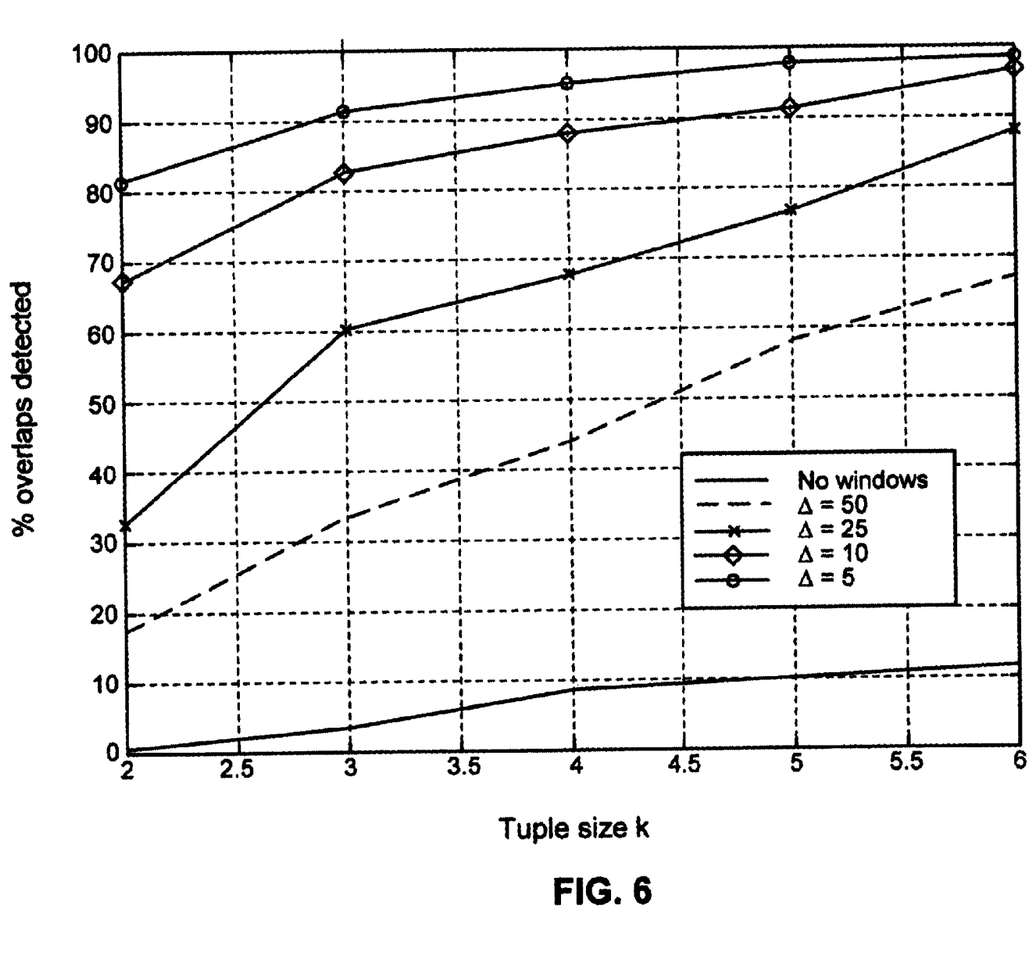
FIG. 6 is a graph showing the results of computations performed to monitor the sensitivity of the present invention as a function of the offset size and the tuple size.

Partitioning the database sequences into overlapping windows advantageously increases the sensitivity of the searching algorithm. Referring now to FIG. 6, there is shown the results of computations performed to monitor the sensitivity of the present invention as a function of the offset size, $\Delta$, and the tuple size, k. The ordinate of FIG. 6 is the percentage of overlaps detected and the abscissa is the tuple size used in the encoding. Each graphed line corresponds to a different offset size $\Delta$ in the sliding window encoding scheme. For example, the solid line corresponds to encoding with no windows, while the dashed line, $\Delta=50$, corresponds to the use of a single offset. Each graphed line in the figure shows the percentage of overlaps correctly detected by the algorithm as a function of the tuple size k. Only overlaps of size greater than or equal than 50 were considered. Thus, as illustrated in FIG. 6, the use of the "sliding window" scheme increases the sensitivity of the present invention. Moreover, as the tuple size k increases, the sensitivity of the present invention also increases.

Referring again to FIG. 4, each database sequence is partitioned into a plurality of overlapping windows and each database sequence window is mapped into a window vector. One skilled in the art will realize that the order in which the database sequences are partitioned into a plurality of windows and the order in which the database sequence windows are mapped into database sequence window vectors is not essential to the invention. In other words, a single database sequence may be partitioned into a plurality of windows and afterwards, each database sequence window may then be used to compute the database sequence window vector corresponding to each database sequence window. In another embodiment, the present invention may first partition all the database sequences into a plurality of database sequence windows, and afterwards compute the corresponding database sequence window vectors. In yet another embodiment, the present invention may partition a database sequence into a first database sequence window and then compute the database sequence window vector for the first database sequence window. The present invention may then partition the database sequence into a second database sequence window and compute the database sequence window vector for the second database sequence window. Thus, one skilled in the art will realize that many options are available for the sequence of steps for partitioning each database sequence into a plurality of overlapping windows and computing the database sequence window vectors corresponding to each database sequence window.

Referring back to FIG. 4, there is shown one embodiment of a method for generating database sequence window vectors for a database sequence. After each database sequence has been partitioned 402 into a plurality of overlapping windows, each database sequence window is then mapped into a window vector. The database sequence window vectors are generated by first determining for each window 404 the frequency of appearance of each k-tuple in a specified database sequence window. A database sequence window vector is then generated 406 for the specified database sequence window. The database sequence window vector indicates the frequency of each k-tuple in that corresponding database sequence window. For a sequence, a k-tuple is a fixed length ordered sequence of elements.

In general, the number of possible k-tuples of length k is $N^k$, where N is the number of unique identifiers from which a sequence can be created and k is the tuple length. For example, from an alphabet of four letters, as in DNA for example, the total number of possible k-tuples is $4^k$. For example, in a sequence generated from the DNA alphabet consisting of {A, C, G, T}, there are 16 possible ordered k-tuples of length k=2: {AA, AC, AG, AT, CA, CC, CG, CT, GA, GC, GG, GT, TA, TC, TG, TT}. In the case of protein sequences, there are 20 letters from which a protein sequence can be created, giving $20^k$ possible k-tuples. Alternate amino-acid alphabets with fewer letters would yield smaller numbers of k-tuples for a fixed k.

Referring to a DNA sequence as an example, the occurrence of each k-tuple in a DNA sequence may be represented by a window vector of length $4^k$. For example, the DNA sequence AACTT contains 2-tuples AA, AC, CT, and TT.

These occurrences of 2-tuples may be represented by the 16-position window vector {1100000100000001}. This window vector corresponds to the ordered representation {AA, AC, AG, AT, CA, CC, CG, CT, GA, GC, GG, GT, TA, TC, TG, TT}. Thus, the 1 in the first position corresponds to the presence of the k-tuple AA, the 1 in the second position corresponds to the presence of the k-tuple AC, the 1 in the eighth position corresponds to the presence of the k-tuple CT, and the 1 in the sixteenth position corresponds to the presence of the k-tuple TT. If a particular k-tuple is not observered in a sequence, then a zero may be placed in the corresponding position in the window vector, as is the case for AG, AT, etc. . . . If a k-tuple occurs more than one time in a sequence, either the number of times that the k-tuple occurs may be recorded in the corresponding position in the window vector or the value "1" may be recorded in the corresponding position in the window vector to indicate that the k-tuple occurs at least once in the sequence. The k-tuple size may be of any length, but for DNA and protein database sequences, k is preferably in the range of $2 \leq k \leq 10$. Thus, window. vectors provide fast and accurate identification of similar sequences with acceptable space requirements.

In one embodiment, a sparse window vector representation may be used to generate the window vectors. Sparse window vector representation allows a user to store only the non-zero entries by storing (index, value) pairs rather than storing the whole vector. For example, consider the DNA sequence ACCGTTGACACCC (SEQ ID NO:1) and suppose that k=2, $\Delta$=2, and W=5. On a disk or larger memory space, all tuples and an index to the beginning of each window are stored. For example, for the above DNA sequence, the following tuple information is stored: AC,CC, CG,GT,TT,TG,GA,AC,CA,AC,CC,CC. In a smaller memory space, such as a RAM, the windows are stored as sparse window vectors such as {(AC, 1), (CC,1), (CG,1), (GT,1)}. Accordingly, when sparse window vectors are used, sparse window vector computations should also be used. In other words, only non-zero entries are used for computations. If an entry is zero in both vectors, it is zero when both vectors are subtracted and hence, no arithmetic needs to be done on entries that are zero. Thus, sparse window vector representation advantageously decreases the amount of memory required for storing the vector windows. Additionally, by using sparse window vector computations, the present invention provides for faster and more efficient computation.

C. Tree-Structure Index Generator

The tree-structured index or database sequence search tree ("SST") organizes the window vectors that represent the database sequences to enable fast and efficient searching of the database sequences. In a preferred embodiment, a binary-tree structured index is used. Alternatively, the tree-structured index may use 3-way branching, 4-way branching, or an arbitrary number of branches at each branch node in the tree. The binary-tree structured index provides for fast searching but requires the largest amount of space. Thus, the branching factor may be selected to best suit the constraints of the available computer hardware.

Figure 7:
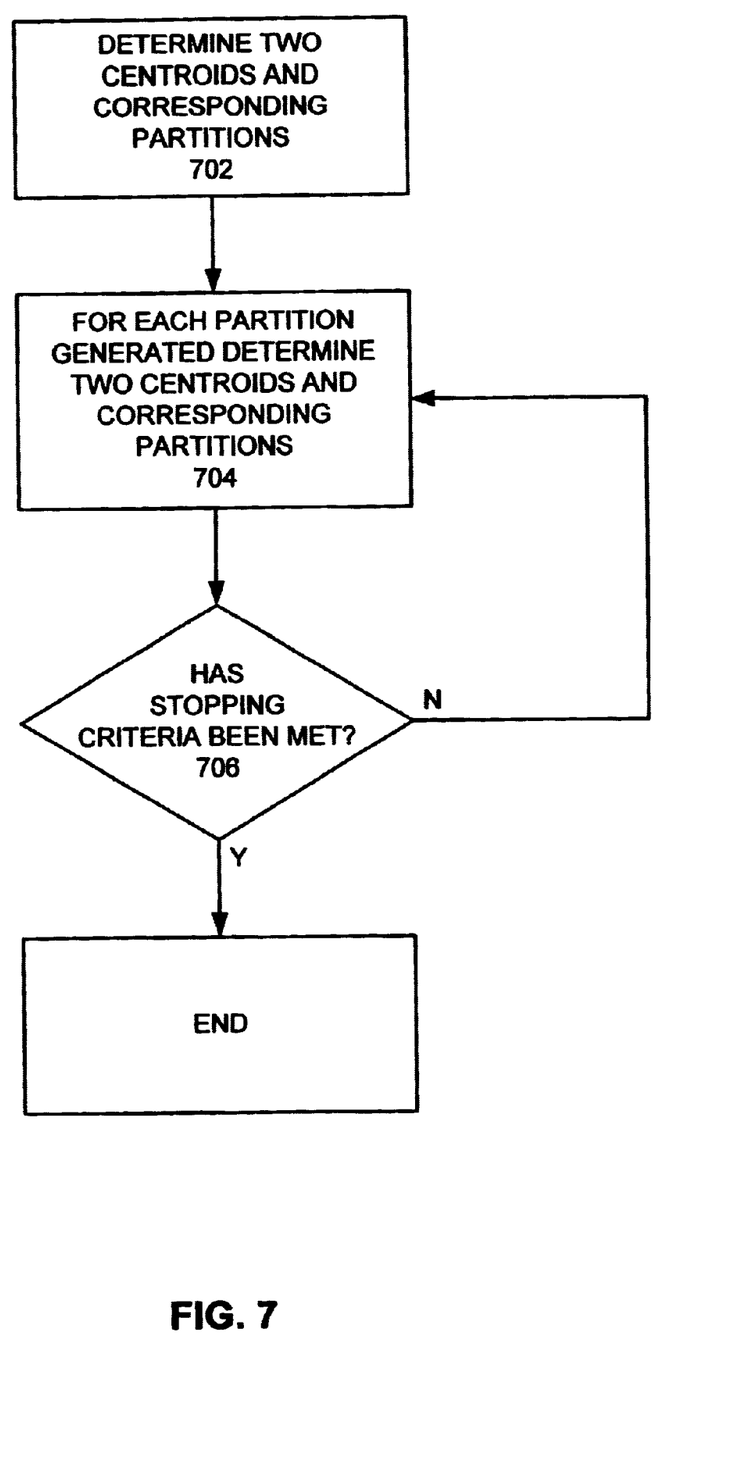
FIG. 7 is a flow chart of the steps of a preferred embodiment for generating a tree-structured index of the database sequences in accordance with the present invention.

The tree-structured index is generated by recursively searching the database sequence window vectors for clusters that provide binary (or higher order) partitions. A variety of methods are available for finding such clusters and building the tree-structured index as would be known to one skilled in the art. In one embodiment, a Tree-Structured Vector Quantization (TSVQ) method using k-means clustering is used to generate the tree-structured index. Referring now to FIG. 7, there is shown a high-level flowchart of a preferred embodiment of the steps for generating a tree-structured index of the database sequence window vectors in accordance with the present invention. First, two centroids and their corresponding partitions of the data are determined 702. In a preferred embodiment, this is done by choosing and designating two points, $a_0$ and $b_0$, in the k-dimensional space as centroids. As used herein, a centroid represents a group of database sequence window vectors. The set of all database sequences closest to each centroid comprises a partition of the k-dimensional space. For example, in a 2-dimensional subspace, the database sequences are partitioned into two disjoint subsets, A and B, by assigning to set A, the sequences closer to $a_0$, and assigning to set B all the other sequences. In other words, for each database sequence, the distance of each sequence from each centroid is calculated and the sequence is assigned to the partition corresponding to the nearest centroid, i.e., the centroid, $a_0$ and $b_0$, which is a minimum distance from the sequence. A new centroid is then determined for each partition by calculating the sum of the distances of all the sequences in the partition from the centroid using the following equations:

$$a_1 = \Sigma_{v \in A} v / |A| \quad |b_1 = \Sigma_{v \in B} v / |B|$$

where A is the set of vectors in Group A, B is the set of vectors in group B, v is a vector, and $\Sigma_{v \in A}$ is the sum of all vectors belonging to set A.

The steps for determining the two centroids are repeated until convergence, that is, until the change in the sum of the distances at each iteration is less than a small threshold, $\epsilon$, or no vectors change partition. In one embodiment, the following equation is used to determine convergence:

$$\|a_0 - a_1\| < \epsilon$$

where $\epsilon$ is preferably a small positive number such as $\epsilon = 10^{-10}$.

If there is no convergence, then $a_0$ is set to $a_1$ and $b_0$ is set to $b_1$ and step 702 is repeated until there is convergence. For each partition generated, two centroids and their corresponding partitions are determined 704 using the steps described above. These steps are repeated 706 until a stopping criterion is met, that is until the number of training sequences in the partitions is less than a user-specified threshold, or the maximum number of terminal nodes is reached. Each of the terminal nodes is a partition of the k-dimensional space and contains a set of sequences that are nearest neighbors to the centroid of that node. In a preferred embodiment, 16-bit finite precision arithmetic is used to compute the centroids. However, one skilled in the art will realize that floating point arithmetic may also be used to compute the centroids.

One skilled in the art will realize that the centroids may be computed using a sample of the windows in the database rather than computing centroids for all the window vectors. For example, in one embodiment, a sample of 500 sequences to estimate two centroids may provide an improvement in the speed for generating a tree-structured index while still providing a relatively low cost in the error rate. Alternatively, one skilled in the art will realize that where higher accuracy is required, a larger sample of sequences for estimating two centroids is preferable. Thus, the use of sampling in generating a tree-structured index enables one to reduce the false negative rate by generating two trees, using different samples, and taking the union of the database sequences in the terminal nodes in which the query sequence falls in the two trees. Both the generation and search of both trees may be done in parallel thereby increasing efficiency and speed. Additionally, in one embodiment, generation of the tree-structured index is completed the first time a leaf size is smaller than 100.

D. Query Sequence and Database Sequence Retrieval

Figure 8:
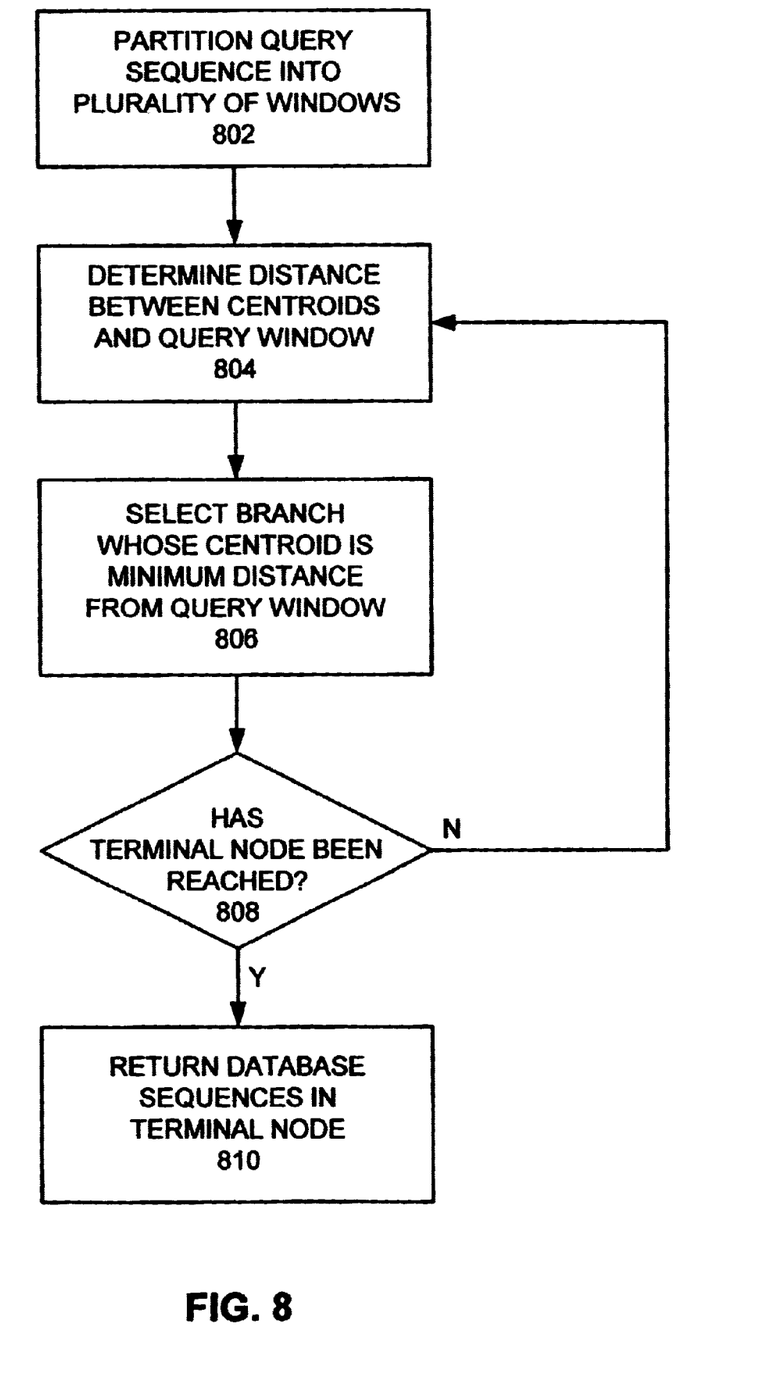
FIG. 8 is a flow chart of the steps of a preferred embodiment for partitioning and using a query sequence to search a tree-structured index in accordance with the present invention.

A query sequence is used to search the tree-structured index to find the database sequences that represent the nearest neighbors of the query sequence. In one embodiment a query sequence refers to a biological sequence, such as a DNA or protein sequence, for which one wishes to find similar sequences in the sequence database. Referring now to FIG. 8, there is shown a high-level flowchart of a preferred embodiment of the steps for partitioning and using the query sequence to search the tree-structured index. Each query sequence is first partitioned 802 into a plurality of windows. Each window of the query sequence has a fixed length W which corresponds to the length of the database sequence windows. In one embodiment, the query sequence may be partitioned into non-overlapping windows. In another embodiment, the query sequence may be partitioned into overlapping windows where the degree of offset among windows is determined by the parameter $\Delta$ as discussed above with respect to window vector generation. Preferably, the query sequence is partitioned using either value for $\Delta$: $\Delta=W$ or $\Delta=W/2$. Each query sequence window is then mapped into a window vector. A query sequence window vector represents the occurrence of each k-tuple in the query sequence window.

Each query sequence window vector is then used to search the tree-structured index by choosing the node whose centroid is the minimum distance between the query sequence window vector and the centroid of that node. The list of database sequences with at least one significant window hit is returned. In other words, the database sequence window vectors in a leaf which are closer to query sequence window vectors than to a given threshold are returned. Additional processing such as alignment of the query sequence to the database sequence with one of the standard alignment tools is also possible. In other words, one can use the Smith-Waterman algorithm to align windows to obtain a better score.

Referring again to FIG. 8, the steps for searching a binary tree-structured index are shown. A search of the tree-structured index begins at the root node of the tree. At each non-terminal node in the tree, each branch is represented in the tree by its centroid. The distance between each centroid and the query window is determined 804. In a preferred embodiment, the distance, d, between two windows, such as a database sequence window, $W_1$, and a query window, $W_2$, is determined by the following equation:

$$d(W_1, W_2) = \|X(W_1) - X(W_2)\|$$

where X(W) refers to the window vector of the window.

The branch whose centroid is the minimum distance from the query sequence window is selected 806. Steps 804 and 806 are repeated through the tree, progressing from the root note towards the terminal nodes, until a terminal node is reached 808. The database sequences in the selected terminal node are the nearest neighbors of the query sequence window. The database sequences representing the nearest neighbors of the query sequence window are then retrieved 810 from the sequence database. In other words, for each query sequence, all database sequences which have a window in common with the query sequence are outputted as a resulting hit.

In another embodiment, the query sequence may be used to search only a portion of the tree-structured index, i.e. a subtree. For example, when searching the tree-structured index using the query sequence window, all query sequence windows may be used to search against a top portion of the tree-structured index. For example, all of the windows of a query sequence may be used to search only the first nine levels of the tree-structured index. Such an embodiment would generate $2^9=512$ groups of windows, where each group contains query sequence windows for the search completed in a different leaf of the top subtree. In such an embodiment, each group is searched against the subtree where it hits. With this embodiment, disk access occurs only when the data associated with each subtree is loaded into memory. One skilled in the art will realized that this embodiment may use an arbitrary number of levels for the subtree and that parallel searching of the tree-structured index may be utilized. For example, after the top subtree is processed, lower level subtrees may be processed using different processors. Thus, the present invention provides a faster and efficient method for searching the tree-structured index.

As the number of database sequences increases, it may become difficult to store all the window vectors in memory. In one embodiment, all vectors are stored on a disk and loaded into RAM as needed. In another embodiment, a caching strategy is used. Due to the in-order nature of the tree-structure generation, a FIFO cache may be used. In such embodiment, a refresh mechanism in which a hit in the cache also moves the vector to the front of the queue may also be used. Additionally, the window vector file should be reordered such that all vectors associated with a certain subtree are contiguous.

E. Performance Results

Tables 1, 2, and 3 below show the performance results of the present invention in comparison with the prior art method BLAST. In the computations, a 1.552 KB piece of genomic DNA was fragmented several times using a Poisson process with average $\Lambda=300$ bp. From the pool of fragments, three sets of 30675, 61350, and 122700 sequences, respectively, were generated. The present invention and the BLAST2 prior art method were used to determine which of the database sequences overlapped. For the computation using the present invention, a window size of length 50 was used and the offset step $\Delta=5$. The computation was repeated for several values of the tuple size k, i.e. k=3, 4, 5, 6. Tables 1, 2, and 3 show the results of the present invention on each of these sets.

TABLE 1

| K | Total | Tree Generation | Query | TPR | FNR | TNR | FPR |
|---|-------|-----------------|-------|-----|-----|-----|-----|
| 3 | 00:10:12 | 00:06:56 | 00:03:16 | 0.893 | 0.107 | 9.9998e−01 | 2.092e−05 |
| 4 | 00:11:37 | 00:07:24 | 00:04:13 | 0.932 | 0.068 | 9.9999e−01 | 1.069e−05 |
| 5 | 00:13:52 | 00:08:24 | 00:05:28 | 0.956 | 0.044 | 9.9999e−01 | 6.642e−06 |
| 6 | 00:23:04 | 00:13:04 | 00:10:00 | 0.963 | 0.037 | 9.9999e−01 | 5.284e−06 |

Table 1 shows the results of the present invention with 30,675 sequences. The time for generating the tree-structured index, for tree search, and the total time are displayed for k=3 to 6. The true positive rate (TPR), false negative rate (FNR), true negative rate (TNR), and false positive rate (FPR) are also displayed.

TABLE 2

| K | Total | Tree Generation | Query | TPR | FNR | TNR | FPR |
|---|---|---|---|---|---|---|---|
| 3 | 00:22:33 | 00:15:36 | 00:06:57 | 0.886 | 0.114 | 9.9999e−01 | 1.842e−05 |
| 4 | 00:26:11 | 00:17:37 | 00:08:34 | 0.926 | 0.074 | 9.9999e−01 | 9.805e−06 |
| 5 | 00:36:49 | 00:19:00 | 00:17:49 | 0.953 | 0.047 | 9.9999e−01 | 6.222e−06 |
| 6 | 00:45:53 | 00:26:37 | 00:19:16 | 0.960 | 0.040 | 9.9999e−01 | 5.018e−06 |

Table 2 shows the results of the present invention with 61,350 sequences. The time for generating the tree-structured index, for tree search, and the total time are displayed for k=3 to 6. The true positive rate (TPR), false negative rate (FNR), true negative rate (TNR), and false positive rate (FPR) are also displayed.

TABLE 3

| K | Total | Tree Generation | Query | TPR | FNR | TNR | FPR |
|---|---|---|---|---|---|---|---|
| 3 | 00:46:56 | 00:31:52 | 00:15:04 | 0.881 | 0.119 | 9.9999e−01 | 1.529e−05 |
| 4 | 00:50:50 | 00:32:50 | 00:18:00 | 0.924 | 0.076 | 9.9999e−01 | 8.404e−06 |
| 5 | 01:08:22 | 00:35:21 | 00:33:01 | 0.951 | 0.049 | 9.9999e−01 | 5.950e−06 |
| 6 | 01:34:50 | 00:52:21 | 00:42:29 | 0.957 | 0.043 | 1.0000e−00 | 4.793e−06 |

Table 3 shows the results of the present invention with 122,700 sequences. The time for generating the tree-structured index, for tree search, and the total time are displayed for k=3 to 6. The true positive rate (TPR), false negative rate (FNR), true negative rate (TNR), and false positive rate (FPR) are also displayed.

Searching the database sequences using the BLAST2 prior art method took 02:03:09, 07:27:47, 28:10:25 for 30,675, 61,350, and 122,700, respectively. Thus, the BLAST2 method yields an average time to bin each sequence of 0.2409, 0.4379, 0.8266 seconds. Thus, with the BLAST2 method there is a linear increase in time per sequence. Thus, as can be seen from the data, the search time required for the present invention is virtually independent of the number of database sequences and is for 122700 sequences 0.00074, 0.0088, 0.0161, and 0.0208 for k=3, 4, 5, 6, respectively. Therefore, for 122,700 sequences the speed-up compared to BLAST2 varies between: 93 for k=3 to 39 for k=6. The search and construction time per sequence using the present invention is 0.0230, 0.0246, 0.0334, and 0.0464 for k=3, 4, 5, 6, respectively. Therefore, for 122700, the speed-up compared to BLAST2 is 35 for k=3 to 17 for k=6.

F. Determination of Optimal Parameters

Figure 9:
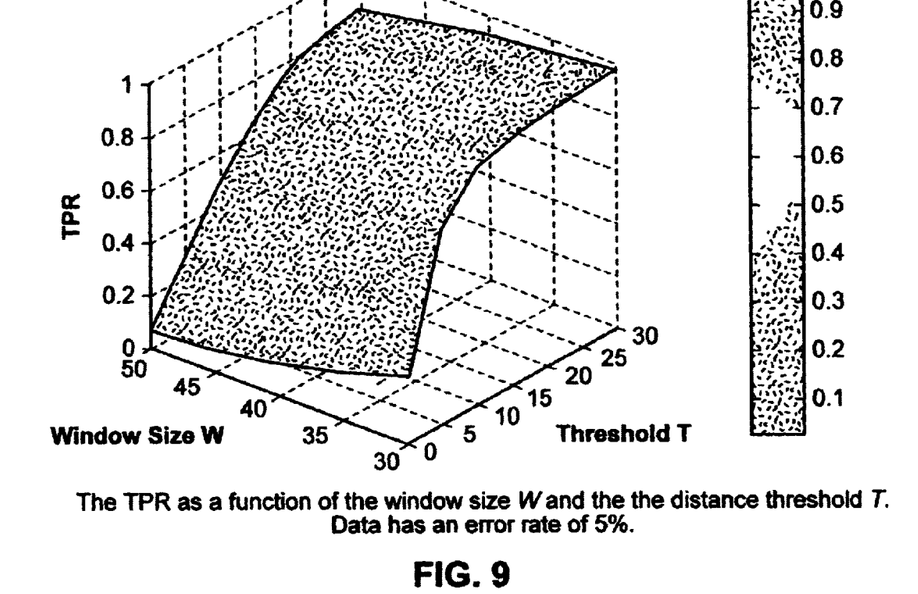
FIG. 9 is a graph showing the true positive rate as a function of the window size.
Figure 10:
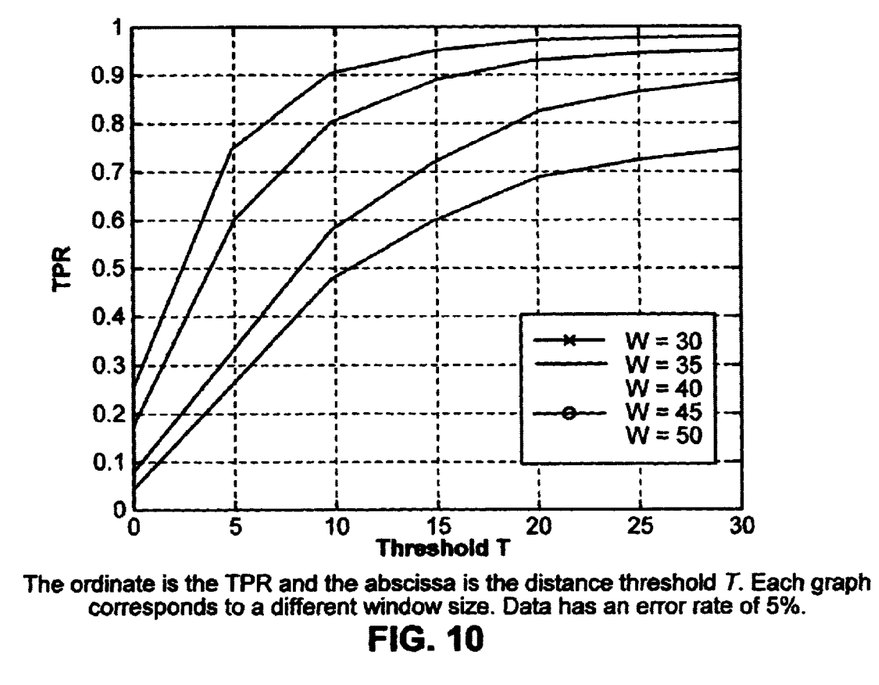
FIG. 10 is a graph showing the true positive rate as a function of window size.

Experiments were performed to determine the optimal values for the threshold T, and the window size, W. The results described below were obtained with data with a 5% error rate. Referring now to FIG. 9, there is shown a graph indicating the true positive rate (TPR) as a function of the window size, W, and the distance threshold T. Cross-sections of this surface, for fixed values of the window size W are presented in FIG. 10. Both figures indicate that the TPR improves as the window size decreases and as the tolerance T increases. Moreover, FIG. 9 shows that the TPR has an asymptotic value as T increases. The asymptotic value increases with a decreasing window size.

Figure 11:
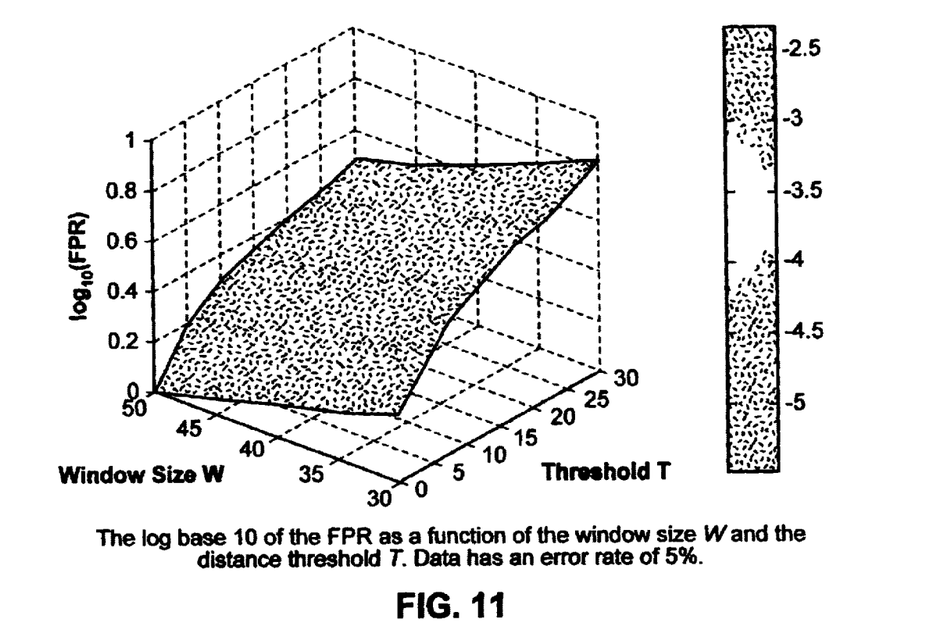
FIG. 11 is a graph showing the false positive rate as a function of the window size and threshold.
Figure 12:
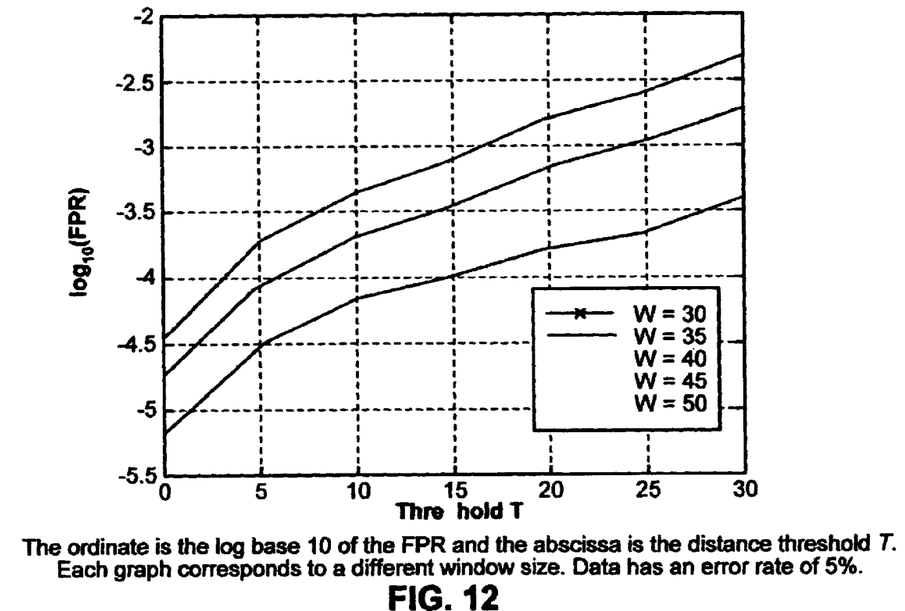
FIG. 12 is a graph showing the false positive rate as a function of the window size and threshold.

The FPR also increases with the tolerance T as indicated by FIGS. 11 and 12 in which the $\log_{10}(FPR)$ is presented. On a logarithmic scale, the growth of the FPR is essentially linear, and the growth rate (the slope) is independent of the window size. Thus, the FPR grows exponentially as a function of T.

Figure 13:
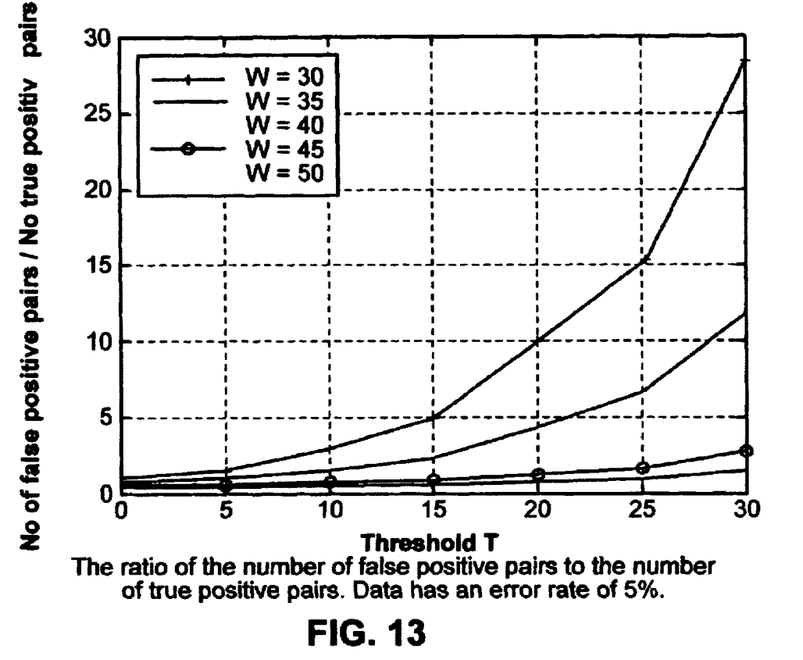
FIG. 13 is a graph showing the ratio of the number of false positive pairs to the number of true positive pairs.

In a preferred embodiment, the window size W and the distance threshold T are chosen such that the TPR is large while the number of false positive pairs remain relatively small. FIG. 13 indicates the ratio of the number of false positive pairs to the number of true positive pairs returned by the present invention. Thus, as can be seen from FIG. 13, for each window size, this ratio increases exponentially with the threshold T. In a preferred embodiment, the parameters W and T are chosen such that their ratio is bounded by 5. Among all possible values for these parameters, the values for which the true positive rate is maximized is desired. The values W=30 and T=15 has a ratio of about 2.5 and a TPR around 0.95, and the values W=35 and T=20 has a ratio less than 5 and a TPR around 0.925.

Figure 14:
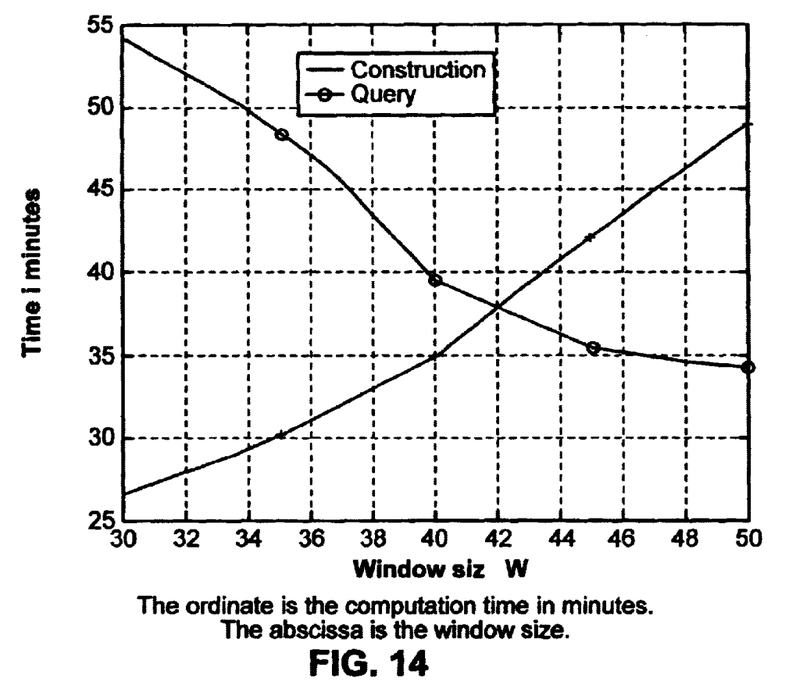
FIG. 14 is a graph showing the time to generate a tree-structured index and the time to search it as a function of window size.

Referring now to FIG. 14, there is shown a graph indicating the time to generate a tree-structured index and the time to search it. The time for generating the tree-structured index increases with the window size. The trend for the search time is reversed. To explain this, one can see that the number of windows in the sequence database N is about $N=n/\Delta$, where n is the total number of nucleotides in the database and $\Delta$ is the offset parameter. Therefore, N is independent of the window size. However, as the length of a window, W, increases, X(W) has more non-zero entries because W contains more tuples. It follows that the time to compute the distance of X(W) has more non-zero entries because W contains more tuples. Accordingly, the time to compute the distance of X(W) to a centroid increases with the length W, and which in turn increases the overall computation time in generating the tree-structured index. In a preferred embodiment, the number of query windows M per query is M=m/M where m is the number of nucleotides in a query. Thus, as the window size increases, the number of query windows decreases so that the time per query also decreases.

We claim:

1. A computer-implemented process for selecting database sequences, the process comprising:
generating a plurality of window vectors representing the content of the database sequences;
generating an index of the window vectors according to positions of the window vectors in a multidimensional space; and
in response to receiving an input query sequence, searching the index using the input query sequence to select database sequences similar to the query sequence.

2. The computer implemented process of claim 1 wherein generating a plurality of window vectors further comprises:
partitioning each database sequence into a plurality of overlapping windows; and
generating a window vector for each window.

3. The computer implemented process of claim 2 wherein each database sequence comprises a finite number of elements, L, and each window begins at position $j*\Delta$ and ends at position $j\Delta+W$, where $j=0, 1 \ldots (L-W)/\Delta$, W is the length of each window, and $\Delta$ is an offset that represents the difference between starting positions of consecutive windows.

4. The computer implemented process of claim 1 wherein generating the index further comprises:
searching the window vectors for clusters providing partitions.

5. The computer implemented process of claim 1 wherein the index is a tree-structured index.

6. The computer implemented process of claim 1 further comprising partitioning the input query sequence into a plurality of non-overlapping windows.

7. The computer implemented process of claim 1 further comprising partitioning the input query sequence into a plurality of overlapping windows.

8. The computer implemented process of claim 1 wherein searching the index using the input query sequence further comprises determining the nearest neighbor of the input query sequence.

9. The computer implemented process of claim 1 wherein searching the index using the input query sequence further comprises:
partitioning the input query sequence into a plurality of windows; and
comparing one of the plurality of windows of the input query sequence with a node of the index.

10. In a computer having a processor and a storage device, the storage device storing a plurality of database sequences in computer-readable form, each database sequence representing a biological sequence of nucleotides, a computer-implemented process for selecting a database sequence in response to an input query sequence representing a biological sequence of nucleotides, the process comprising:
generating a plurality of window vectors representing the content of the database sequences;
generating a tree-structured index of the database sequences according to positions of the window vectors in a multidimensional space; and
using the input query sequence to search the tree-structured index to identify database sequences similar to the query sequence.

11. The computer-implemented process of claim 10 wherein generating a plurality of window vectors further comprises:
partitioning each database sequence into a plurality of overlapping windows, each window comprising a plurality of k-tuples; and
mapping the occurrence of each k-tuple in each window into a window vector.

12. The computer-implemented process of claim 11 wherein each of the plurality of windows has a fixed length W and the overlap of the plurality of windows being determined by a parameter $\Delta$.

13. The computer implemented process of claim 10 further comprising partitioning the input query sequence into a plurality of windows.

14. The computer implemented process of claim 10 wherein the tree-structured index of the database sequences is generated using Tree-Structured Vector Quantization.

15. The computer implemented process of claim 10 wherein the tree-structured index is a binary-tree index.

16. A computer-implemented process for generating a tree-structured index representing database sequences, the process comprising:

partitioning each database sequence into a plurality of overlapping windows;

mapping each window into a window vector that represents the content of the window; and generating the tree-structured index for the overlapping windows according to positions of the window vectors in a multidimensional space.

17. The computer implemented process of claim 16 wherein each window has a fixed length W and an offset $\Delta$, each window beginning at position $j*\Delta$ and ending at position $j*(\Delta+W)$, where $j=0, 1, 2, 3 \ldots$.

18. The computer implemented process of claim 16 wherein the tree-structured index is generated using Tree-Structured Vector Quantization.

19. The computer implemented process of claim 16 wherein the tree-structured index is a binary-tree index.

20. The computer implemented process of claim 16 further comprising:

in response to receiving a query sequence, searching the tree-structured index using the query sequence to identify database sequences similar to the query sequence.

21. In a computer-implemented system comprising a plurality of database sequences, a system for generating a tree-structure index that represents the database sequences, the system for generating a tree structure index comprising:

a computer-readable medium for storing program instructions for execution by a processor;

a window vector generating component, stored on the computer-readable medium and executable by the processor, for mapping each database sequence into a window vector, the window vector representing the content of the database sequence; and a tree-structure index generator, stored on the computer-readable medium and executable by the processor, for generating a tree-structure index of the window vectors in accordance with positions of the window vectors in a multidimensional space.

22. The system for generating a tree structure index of claim 21 wherein the window vector generating component further comprises:

a window partitioning component, stored on the computer-readable medium and executable by the processor, for partitioning each database sequence into a plurality of windows; and a window vector mapping component, stored in the computer-readable medium and executable by the processor for mapping each window into a window vector.

23. A computer-implemented system for selecting database sequences from a database comprising a plurality of sequences stored in electronic form, the system comprising:

a computer processor for executing programmed instructions and for storing and retrieving data;

an input device, coupled to the processor, for receiving a query sequence;

a program memory, coupled to the processor, for storing program instructions for execution by the processor;

a window vector generating component, stored in the computer readable medium and executable by the processor, for mapping each database sequence into a window vector, where the window vector represents the content of the database sequence;

a tree-structure index generator, executable by the processor in accordance with program instructions in the program memory, for generating a tree-structure index that represents the database sequences, where the tree-structure index is generated in accordance with positions of the window vectors in a multi-dimensional space;

a query sequence partitioning component, executable by the processor in accordance with program instructions in the program memory, for partitioning a query sequence into a plurality of windows; and a retrieval component, executable by the processor in accordance with program instructions in the program memory, for retrieving database sequences from the database that are similar to the query sequence.

24. A computer readable memory, for use with a processor and a plurality of database sequences, the memory storing a computer program executable by the processor for configuring and controlling the processor to generate a tree-structured index that represents the database sequences, by performing the steps of:

partitioning each database sequence into a plurality of overlapping windows;

for each window, generating a window vector representing the content of the window; and generating a tree-structured index of the window vectors according to positions of the window vectors in a multidimensional space.

25. A computer readable memory, for use in a computer system comprising a processor and a database storing a plurality of database sequences in computer-readable form, and for selecting database sequences from the database in response to a query sequence, the computer readable memory storing:

a window vector generating component, stored in the computer readable medium and executable by the processor, for mapping each database sequence into a window vector, where the window vector represents the content of the database sequence;

a tree-structured index generator, executable by the processor in accordance with program instructions in the memory, for generating a tree-structured index that represents the database sequences, where the tree-structure index is generated in accordance with positions of the window vectors in a multidimensional space;

a query sequence partitioning component, executable by the processor in accordance with program instructions in the memory, for partitioning a query sequence into a plurality of windows; and a retrieval component, executable by the processor in accordance with program instructions in the memory, for retrieving database sequences from the database that are similar to the query sequence.

26. The computer implemented process of claim 1, wherein searching the index further comprises:

generating at least one vector representing the query sequence;

identifying a group of window vectors in the index that are closest in the multidimensional space to a vector representing the query sequence.

27. The computer implemented process of claim 26 further comprising returning the database sequences that correspond to the identified window vector as a search result.

28. The computer implemented process of claim 1 where each window vector represents whether its corresponding database sequence includes one or more select elements.

* * * * *